(12) United States Patent
Li et al.

(10) Patent No.: US 12,226,758 B2
(45) Date of Patent: Feb. 18, 2025

(54) RANEY COPPER CATALYST AS WELL AS PREPARATION METHOD AND USE THEREOF

(71) Applicant: NINGBO INSTITUTE OF MATERIALS TECHNOLOGY & ENGINEERING, CHINESE ACADEMY OF SCIENCES, Ningbo (CN)

(72) Inventors: Bin Li, Ningbo (CN); Bo Yan, Ningbo (CN); Hongfeng Yin, Ningbo (CN); Jie Zhang, Ningbo (CN); Shenghu Zhou, Ningbo (CN)

(73) Assignee: NINGBO INSTITUTE OF MATERIALS TECHNOLOGY AND ENGINEERING, CHINESE ACADEMY OF SCIENCES, Ningbo (CN)

( * ) Notice: Subject to any disclaimer, the term of this patent is extended or adjusted under 35 U.S.C. 154(b) by 666 days.

(21) Appl. No.: 17/596,425

(22) PCT Filed: Nov. 11, 2020

(86) PCT No.: PCT/CN2020/127944
§ 371 (c)(1),
(2) Date: Dec. 10, 2021

(87) PCT Pub. No.: WO2022/099489
PCT Pub. Date: May 19, 2022

(65) Prior Publication Data
US 2022/0355276 A1 Nov. 10, 2022

(51) Int. Cl.
*B01J 25/00* (2006.01)
*B01J 35/40* (2024.01)
*B01J 37/08* (2006.01)

(52) U.S. Cl.
CPC ............... *B01J 25/00* (2013.01); *B01J 35/40* (2024.01); *B01J 37/08* (2013.01)

(58) Field of Classification Search
CPC .. B01J 25/00; B01J 35/40; B01J 37/08; C22C 1/0425; C22C 9/01
USPC ........ 502/301, 327, 331, 346, 355; 420/469, 420/489
See application file for complete search history.

(56) References Cited

U.S. PATENT DOCUMENTS

| | | | | |
|---|---|---|---|---|
| 3,544,485 A | * | 12/1970 | Kuroda | ............... B01J 25/00 568/903 |
| 3,929,673 A | | 12/1975 | Hoffmann et al. | |
| 3,941,720 A | | 3/1976 | Hoffmann et al. | |
| 4,386,018 A | | 5/1983 | Merger et al. | |
| 5,536,694 A | * | 7/1996 | Schuetz | ............... B01J 35/613 502/301 |
| 5,733,838 A | | 3/1998 | Vicari et al. | |
| 6,207,865 B1 | | 3/2001 | Breitscheidel et al. | |
| 2003/0120116 A1 | * | 6/2003 | Ostgard | ............... B01J 35/58 502/301 |

FOREIGN PATENT DOCUMENTS

| | | | | |
|---|---|---|---|---|
| CA | 2881474 A1 | * | 2/2014 | ............. B01J 25/00 |
| CN | 1064511 A | | 9/1992 | |
| CN | 101530804 A | | 9/2009 | |
| CN | 101530804 A1 | * | 9/2009 | ............. B01J 25/00 |
| CN | 1926084 B | | 8/2010 | |
| CN | 102603681 A | | 7/2012 | |
| CN | 102617519 A | | 8/2012 | |
| CN | 102617519 A1 | * | 8/2012 | ............. B01J 23/755 |
| CN | 104513130 A | | 4/2015 | |
| CN | 104513136 A1 | * | 4/2015 | ............. B01J 31/06 |
| CN | 105481647 A | | 4/2016 | |
| CN | 105481647 A1 | * | 4/2016 | ............. B01J 25/00 |
| CN | 107952450 A | | 4/2018 | |
| CN | 109317164 A | | 2/2019 | |
| EP | 0734765 A1 | * | 10/1996 | ............. B01J 25/02 |
| WO | 9003801 A1 | | 4/1990 | |

OTHER PUBLICATIONS

English translation of Written Opinion for PCT/CN2020/127944. (Year: 2021).*

* cited by examiner

*Primary Examiner* — Patricia L. Hailey
(74) *Attorney, Agent, or Firm* — Bayramoglu Law Offices LLC

(57) ABSTRACT

A Raney copper catalyst, a preparation method and use thereof are provided. The Raney copper catalyst includes aluminum, copper and a metal promoter, wherein the metal promoter comprises a combination of one or more of Ni, Fe, Mo, Co, Ag, Pd, Pt, Au and other elements. The preparation method includes performing high-temperature melting on a mixture containing a copper/aluminum alloy and the metal promoter to obtain a mixed metal cured compound, then smashing the mixed metal cured compound to obtain a catalyst precursor, and subsequently activating to obtain the Raney copper catalyst. The Raney copper catalyst exhibits a capability on hydrogenation reaction based on synergistic effects between metal copper and different promoter metals. Compared with the Raney copper catalyst without metal promoters, when used for preparing 1,3-propanediol through hydrogenation of 3-hydroxypropionaldehyde aqueous solution, the Raney copper catalyst is higher in activity and better in stability.

17 Claims, No Drawings

RANEY COPPER CATALYST AS WELL AS PREPARATION METHOD AND USE THEREOF

CROSS REFERENCE TO RELATED APPLICATIONS

This application is the national stage entry of International Application No. PCT/CN2020/127944, filed on Nov. 11, 2020, the entire contents of which are incorporated herein by reference.

TECHNICAL FIELD

The present invention relates to a Raney copper catalyst, particularly to a novel Raney copper catalyst in which is added with a metal promoter as well as a preparation method thereof and use of this novel Raney copper catalyst in preparation of 1,3-propanediol through hydrogenation of 3-hydroxypropionaldehyde, belonging to the technical field of catalyst preparation and application.

BACKGROUND

Hydrogenation of 3-hydroxypropionaldehyde is an important way to industrially prepare 1,3-propanediol. 1,3-propanediol is a widely used compound, which is mainly applied to synthesis of plasticizers, detergents, preservatives, emulsifiers, polyesters and polyurethanes and can be also used as anti-freezing agent, solvent, protecting agent and the like. The most important application of 1,3-propanediol is as a main raw material for producing poly(1,3-propanediol terephthalate) fiber (PTT). Both having the performance of polyethylene terephthalate and good rebound resilience and anti-fouling performance of nylon, the PTT fiber is widely applied in the fields such as carpets, engineering plastics and garment fabrics, and has become a hot spot in developing synthetic fiber in the world recently. 3-hydroxypropionaldehyde can be prepared through hydration of acraldehyde, hydroformylation of ethylene oxide and other processes. Since 3-hydroxypropionaldehyde is extremely instable, many side reactions such as polymerization, condensation and decomposition are likely to occur during the hydrogenation. Furthermore, these side reactions can be aggravated while the temperature rises. Thus, choosing a catalyst with high activity and high selectivity to make the hydrogenation reaction carried out at a reaction temperature as low as possible is very important. At present, catalysts for preparing 1,3-propanediol through hydrogenation of 3-hydroxypropionaldehyde, which have been reported, approximately include (1) Raney nickel catalysts; (2) supported catalysts based on platinum, palladium or ruthenium as an active component; (3) catalysts based on nickel as a main active component. However, Raney copper as the hydrogenation catalyst which is used in preparing 1,3-propanediol through hydrogenation of 3-hydroxypropionaldehyde is rarely reported.

At present, at home and abroad, there are several existing patents and References concerning application of Raney copper catalysts in hydrogenation of compounds. For example, the patents are as follows: C.N. Pat. 10645115A, C.N. Pat. 107952450A, C.N. Pat. 1926084B, D.E. Pat. 1998507079, U.S. Pat. No. 6,207,865B1, 4,386,018A, 5,733,838A, W.O. Pat. 199003801A1, etc.

The patent CN1064511A refers to a Zn-doped Raney copper catalyst and use thereof in a route for hydrogenation of vinyl acetylene. The reaction conditions of the process route are as follows: the pressure of hydrogen is 0.9 MPa, the temperature is 38-50° C., a molar ratio of hydrogen to alkyne is 2.6:1, and the liquid mass space velocity is 12 h$^{-1}$. Under these conditions, the conversion rate of vinyl acetylene is approximately 99.9%. This invention shows that the Zn-doped Raney copper catalyst has a good hydrogenation performance in a double bond/triple bond hydrogenation reaction.

The patent WO199003801A1 relates to a method for applying a Raney copper catalyst to hydrogenation of a carbonyl compound. On the presence of a catalyst, the hydrogenation reaction can be carried out in a fluidized bed flowing up and down. In the fluidized bed flowing up and down simultaneously, the hydrogenation reaction is often carried out at the temperature of 100-140° C. under the pressure of 25-100 bar. The conversion and selectivity of the carbonyl compound especially 3-hydroxypropionaldehyde are 86% and 89%, respectively. This patent also illustrates that the Raney copper catalyst is feasible in a process route for preparing 1,3-propanediol through hydrogenation of 3-hydroxypropionaldehyde.

Although the Raney copper catalysts with addition or without addition of metal promoters have been reported in some patents, industrial application of these catalysts in preparation of 1,3-propanediol through hydrogenation of 3-hydroxypropionaldehyde are not involved. Meanwhile, in the route of hydrogenation, they usually have some defects, such as low reaction conversion rate and selectivity. Thus, it is necessary to invent a catalyst which is efficient and low in cost.

SUMMARY

The main objective of the present application is to provide a novel Raney copper catalyst added with a metal promoter and a preparation method thereof in order to overcome the defects in the existing technology.

Another objective of the present application is to provide use of a novel Raney copper catalyst in preparation of 1,3-propanediol through hydrogenation of 3-hydroxypropionaldehyde.

In order to realize the above objectives, the technical solutions adopted by the present application includes:

The embodiments of the present application provide a novel Raney copper catalyst, mainly comprising aluminum, copper and a metal promoter, wherein the metal promoter comprises a precious metal promoter and/or a non-precious metal promoter, the non-precious metal promoter comprises a combination of one or more than two of Ni, Fe, Mo and Co, and the precious metal promoter comprises a combination of one or more than two of Ag, Pd, Pt and Au.

The embodiments of the present application also provide a preparation method of the above novel Raney copper catalyst, comprising:
  melting a mixture containing copper/aluminum alloy and the metal promoter in a protective atmosphere, and then standing at room temperature to obtain a mixed metal cured compound;
  smashing the mixed metal cured compound to obtain a catalyst precursor; and
  activating the catalyst precursor to obtain the novel Raney copper catalyst.

In some preferred embodiments, the activating comprises:
  a reaction basket body loaded with the catalyst precursor is placed into a reaction container, water and an organic additive are added into the reaction container, then the reaction container is sealed, and the basket body is maintained to vertically rotate;

an alkali aqueous solution is dropwise added into the reaction container, and meanwhile the reaction basket continues to be maintained to vertically rotate, thereby activating as indicated above.

The embodiments of the present application also provide use of the above novel Raney copper catalyst in preparation of 1,3-propanediol through hydrogenation of 3-hydroxypropionaldehyde.

Correspondingly, the embodiments of the present application also provide a method for preparing 1,3-propanediol, comprising:

carrying out hydrogenation reaction on a reaction system containing the novel Raney copper catalyst and aqueous solution of 3-hydroxypropionaldehyde in a hydrogen atmosphere to prepare 1,3-propanediol.

Compared with the existing technology, the present application at least has the beneficial effects:

The preparation method of the catalyst for preparing 1, 3-propanediol through hydrogenation of 3-hydroxypropionaldehyde provided by the present application is innovative. Through the introduction of organic additives in the process of catalyst preparation, a synergistic effect occurs between metal copper and promoter metal, so as to (1) promoting hydrogenation conversion of 3-hydroxypropionaldehyde; (2) improving the selectivity of hydrogenation of 3-hydroxypropionaldehyde and reducing side reactions; (3) realizing the high selectivity of product 1,3-propanediol; and (4) improving the utilization rate of precious metals. The details are as follows:

When the promoter is any one or more of non-precious metal elements such as Ni, Fe, Mo or Co, a synergistic effect occurs between the non-precious metal element and the main active metal Cu in the catalyst. For example, compared with the Raney copper and Raney nickel catalysts widely used in industry, the nickel-doped Raney copper catalyst is greatly improved in terms of the conversion rate of 3-hydroxypropionaldehyde and the selectivity of 1,3-propanediol;

When the promoter is any one or more precious metal elements such as Ag, Pd, Pt or Au, a synergistic effect occurs between the precious metal elements and the main active metal Cu in the catalyst. On the one hand, an intermetallic force between Cu and Al is promoted and the hydrogenation is propelled. On the other hand, the precious metal, as a second active center of hydrogenation reaction, improves the activity of the catalyst. For example, compared with the industrial Raney copper catalyst and Pd-doped Raney nickel catalyst, the conversion rate of 3-hydroxypropionaldehyde and the selectivity of product 1,3-propanediol are both significantly improved;

When the promoter is a combination of any one or more of non-precious metal elements such as Ni, Fe, Mo or Co and any one or more of precious metal elements such as Ag, Pd, Pt or Au, the non-precious metal M1 and precious metal in the catalyst not only have a synergistic effect with the main active metal Cu to strengthen the intermetallic force between Cu and Al, and meanwhile the synergistic effect occurs between non-precious metals and precious metals. For example, compared with Pd-doped Raney copper catalyst and Mo-doped Raney copper catalyst, the Mo and Pd-doped Raney copper catalyst has higher conversion rate of 3-hydroxypropionaldehyde, higher selectivity of product 1,3-propanediol and higher precious metal utilization rate.

In conclusion, for hydrogenation reaction of 3-hydroxypropionaldehyde, the catalyst prepared by this method has the advantages of high activity, high selectivity, high stability, mild reaction conditions and relatively large catalyst particles, and are easily separated from reactants.

DETAILED DESCRIPTION OF THE EMBODIMENTS

In order to overcome the defects in the existing technology, the inventors of this case propose the technical solution of the present application through long-term research and lots of practice. The present application mainly provides a catalyst for producing 1,3-propanediol through hydrogenation of 3-hydroxypropionaldehyde. This catalyst is a Raney copper catalyst with a metal promoter. This catalyst mainly consists of metal aluminum, copper and one or more metal promoters (Ni, Fe, Mo, Co, Ag, Pd, Pt, Au, etc.). Based on the synergistic effect between metal copper and different promoter metals, this catalyst exhibits good capability on hydrogenation reaction. Next, the technical solution, implementation process and principle and the like will be further explained.

A novel Raney copper catalyst provided by one aspect of the embodiments of the present application mainly comprises aluminum, copper and a metal promoter, wherein the metal promoter comprises a precious metal promoter and/or a non-precious metal promoter, the non-precious metal promoter comprises a combination of one or more than two of Ni, Fe, Mo and Co, and the precious metal promoter comprises a combination of one or more than two of Ag, Pd, Pt and Au.

In some preferred embodiments, the novel Raney copper catalyst is an improved Raney copper catalyst Al—Cu-M, in which the component M is the added promoter metal.

The design mechanism of the present application is that through the introduction of organic additives in the process of catalyst preparation, a synergistic effect occurs between metal copper and promoter metal, so as to (1) promoting hydrogenation conversion of 3-hydroxypropionaldehyde; (2) improving the selectivity of hydrogenation of 3-hydroxypropionaldehyde and reducing side reactions; (3) realizing the high selectivity of product 1,3-propanediol; and (4) improving the utilization rate of precious metals.

In some preferred embodiments, the metal promoter M in the novel Raney copper catalyst includes but is not limited to a combination of any one or more of Ni, Fe, Mo, Co, Ag, Pd, Pt, Au and other metal elements.

In some preferred embodiments, the content (support amount) of the metal promoter in the novel Raney copper catalyst is about 0.1 wt %-10 wt %.

In some preferred embodiments, the content (support amount) of the precious metal promoter added in the novel Raney copper catalyst is 0.1 wt %-1 wt %.

Further, the content (support amount) of the non-precious metal promoter in the novel Raney copper catalyst is 1 wt %-10 wt %.

In some preferred embodiments, a mass ratio of aluminum to copper in the novel Raney copper catalyst is 1:(0.5-1), that is, Al:Cu=1:(0.5-1).

Further, a mass ratio of Al to Cu in the novel Raney copper catalyst is 20:80-80:20, preferably, 33:66-66:33.

In some preferred embodiments, there are several proportions of support amounts of metal promoters in the novel Raney copper catalyst:
(1) when the metal promoter M is selected from non-precious metal promoters, that is, M is any one or more of non-precious metal elements such as Ni, Fe, Mo or Co, a mass ratio of aluminum to copper to metal promoter in the novel Raney copper catalyst is 1:(0.5-1):(0.02-0.22), that is, Al:Cu:M=1:(0.5-1):(0.02-0.22);
when the promoter is any one or more of non-precious metal elements such as Ni, Fe, Mo or Co, a synergistic effect occurs between non-precious metal element and main active metal Cu. For example, compared with Raney copper and Raney nickel catalysts widely used in industry, the nickel-doped Raney copper catalyst significantly improves the conversion rate of 3-hydroxypropionaldehyde and the selectivity of 1,3-propanediol.
(2) when the metal promoter M is selected from precious metal promoters, that is, M is any one or more of precious metal elements such as Ag, Pd, Pt or Au, a mass ratio of aluminum to copper to metal promoter in the novel Raney copper catalyst is 1:(0.5-1):(0.002-0.02), that is, Al:Cu:M=1:(0.5-1):(0.002-0.02);
when the promoter is any one or more of precious metal elements such as Ag, Pd, Pt or Au, a synergistic effect occurs between non-precious metal element and main active metal Cu in the catalyst. On the one hand, an intermetallic force between Cu and Al is promoted, and hydrogenation is driven. On the other hand, the precious metal improves the activity of the catalyst as a second active center of hydrogenation reaction. For example, compared with the industrial Raney copper catalyst and Pd-doped Raney nickel catalyst, the conversion rate of 3-hydroxypropionaldehyde and the selectivity of product 1,3-propanediol are significantly improved.
(3) when the metal promoter M is selected from a combination of a precious metal promoter and a non-precious metal promoter, that is, M is a combination of an any one or more of non-precious metal element M1 such as Ni, Fe, Mo or Co and any one or more of precious metal element M2 such as Ag, Pd, Pt or Au, a mass ratio of aluminum to copper to non-precious metal promoter to precious metal promoter in the novel Raney copper catalyst is 1:(0.5-1):(0.02-0.24):(0.002-0.02), that is, Al:Cu:M1:M2=1:(0.5-1):(0.02-0.24):(0.002-0.02);
when the promoter is a combination of any one or more of non-precious metal element M1 such as Ni, Fe, Mo or Co and any one or more of precious metal element M2 such as Ag, Pd, Pt or Au, synergistic effects occur between non-precious metal element M1 and precious metal M2 as well as main active metal Cu in the catalyst, and meanwhile a synergistic effect occurs between non-precious metal element M1 and precious metal M2. For example, compared with the Pd-doped Raney copper catalyst and the Raney nickel catalyst, the Mo/Pd-doped Raney copper catalyst has higher conversion of 3-hydroxypropionaldehyde and higher selectivity of 1,3-propanediol.

In some preferred embodiments, the novel Raney copper catalyst is shaped like an irregular geometric block.

Further, since the hydrogenation speed of 3-hydroxypropionaldehyde is controlled by internal diffusion, relatively small catalyst particles have a promotion effect on the reaction. Meanwhile, it is considered that the catalyst is easily separated from reaction products, so the catalyst has a particle size of 0.1-5 mm, preferably 0.1-1.5 mm, especially preferably 0.5-1.5 mm.

The Raney copper catalyst added with the metal promoter provided by the present application meets the previous industrial requirements, and meanwhile has the following advantages: (1) high activity; (2) high selectivity; (3) low preparation cost; and (4) easy separation, compared with the traditional industrial Raney copper catalyst.

Another aspect of the embodiments of the present application also provides a preparation method of a novel Raney copper catalyst as described above, comprising:
melting a mixture containing copper/aluminum alloy and the metal promoter in a protective atmosphere, and then standing at room temperature to obtain a mixed metal cured compound;
smashing the mixed metal cured compound to obtain a catalyst precursor; and
activating the catalyst precursor to obtain the novel Raney copper catalyst.

In some preferred embodiments, the temperature of high-temperature melting is 500-3000° C., preferably 650-1500° C.

In some preferred embodiments, the smashing comprises: the mixed metal cured compound is cracked and ground to a selected size to obtain the catalyst precursor.

Further, the selected size is 3-140 mesh, preferably, 13-35 mesh.

In some preferred embodiments, the activating comprises:
a reaction basket body loaded with the catalyst precursor is placed into a reaction container, water and an organic additive are added into the reaction container, then the reaction container is sealed, and the basket body is maintained to vertically rotate;
an alkali aqueous solution is dropwise added into the reaction container, and meanwhile the reaction basket continues to be maintained to vertically rotate, thereby activating at room temperature.

Further, the preparation method also comprises: after the activating is ended, the obtained catalyst product is taken out, and washed with water to a pH value of 7-8.

Where, in some more preferred embodiments, a method for preparing a novel Raney copper catalyst for preparing 1,3-propanediol through hydrogenation of 3-hydroxypropionaldehyde specially comprises the following steps:
(1) in a nitrogen atmosphere, a proper amount of copper/aluminum alloy powder and metal promoter M powder are weighed and evenly mixed, molten at a high temperature, and subjected to standing at room temperature to obtain a cured compound of mixed metal powder;
(2) the cured compound in step (1) is cracked and ground to a proper size as a catalyst precursor; and the catalyst precursor is placed in a basket;
(3) the basket loaded with the catalyst precursor in step (2) is introduced into a middle neck of a three-necked flask, and a large amount of deionized water and a proper amount of organic additive are added in turn;
(4) after the three-necked flask is sealed and blown with nitrogen, at the same time, the basket in step (3) is maintained to vertically rotate;
(5) during the period of time, a proper amount of alkali aqueous solution was dropwise added into the three-necked flask;
(6) the basket was continued to keep rotating, and activating until no hydrogen is generated in the three-necked flask;

(7) after the activating is ended, the obtained catalyst particles are taken out, and washed with deionized water to an appropriate pH value;

(8) the prepared catalyst is sealed with deionized water and used for a reaction that 1,3-propanediol is prepared through hydrogenation of 3-hydroxypropionaldehyde.

Further, in the above step (1), a mass ratio of aluminum to copper in the copper/aluminum powder is 20:80-80:20, preferably 33:66-66:33.

Further, in the above step (1), the melting temperature of the mixed metal powder is 500-3000° C., preferably 650-1500° C.

Further, in the above step (2), the proper size is 3-140 mesh, preferably, the particle size is 13-35 mesh.

Further, in the above step (3), the organic additive is selected from aliphatic polyols such as adipic polyester diol, but is not limited thereto.

Further, in the above step (3), the addition amount of the deionized water must allow the catalyst precursor to be immersed to ensure that the catalyst precursor particles are always under the liquid level.

Further, in the above step (4), the rotation speed of the basket is 200-1000 rpm, preferably 500-800 rpm.

Further, in the above step (4), the catalyst is activated for 2-8 h once, preferably 4-6 h.

Further, in the above step (5), the alkali is one of sodium hydroxide and potassium hydroxide.

Further, in the above step (5), the mass fraction of the alkali aqueous solution is 40-60%.

Further, in the above step (5), a mass ratio of added alkali aqueous solution to mixed metal particles is 3:1-5:1, preferably 3.5:1-4:1.

Further, in the above step (6), the pH value is preferably 7-8.

Further, the preparation method also comprises: after the activating is ended, the obtained catalyst product is taken out, and washed with water to a pH value of 7-8.

Another aspect of the embodiments of the present application also provides use of a novel Raney copper catalyst as described above in preparation of 1,3-propanediol through hydrogenation of 3-hydroxypropionaldehyde.

Compared with the Raney copper catalyst with no addition of metal promoters, when this catalyst is used for preparation of 1,3-propanediol through hydrogenation of 3-hydroxypropionaldehyde aqueous solution, it is higher in activity and better in selectivity and better in stability, and this catalyst has relatively large particles and is easily separated from reaction products.

Correspondingly, another aspect of the embodiments of the present application also provides a method for preparing 1,3-propanediol, comprising:

carrying out hydrogenation reaction on a reaction system containing the novel Raney copper catalyst and aqueous solution of 3-hydroxypropionaldehyde in a hydrogen atmosphere to prepare 1,3-propanediol.

In some preferred embodiments, the content of the catalyst in the reaction system is 0.2-5.0 wt %.

In some preferred embodiments, the process conditions of the hydrogenation reaction are as follows: the temperature of the hydrogenation reaction is 40-150° C., the time of the hydrogenation reaction is 60-120 min, the pressure of the hydrogenation reaction is 3.0-10.0 MPa, and the concentration of the aqueous solution containing 3-hydroxypropionaldehyde is 5-15 wt %.

Further, the hydrogenation reaction is often carried out in an autoclave. A proper stirring speed is applied when in reaction, which facilitates the reaction. the hydrogenation speed of 3-hydroxypropionaldehyde is proportioned to a partial pressure of hydrogen and hydrogenation temperature. The present application recommends the following reaction conditions: the weight percentage concentration of the raw material 3-hydroxypropionaldehyde aqueous solution is 5-15%, the hydrogenation temperature is 40-150° C., the hydrogen pressure is 3.0-10.0 MPa, the amount of the catalyst is 0.2-5.0% by weight of the catalyst in the reaction solution.

These metal-doped Raney copper catalysts are used in a process route for producing 1,3-propanediol through hydrogenation of 3-hydroxypropionaldehyde. The catalyst exhibits higher activity, higher selectivity and better catalyst stability. In addition, the size of the catalyst particles is relatively large, so the catalyst is easily separated from reaction products. The catalyst effectively solves the problems existing in the field of propylene glycol production.

According to the above reaction conditions, when the hydrogenation time is 60-120 min, the conversion rate of 3-hydroxypropionaldehyde and the selectivity of 1,3-propanediol both reach 100%. After the reaction is ended, the catalyst can be easily separated from reaction products via conventional solid-liquid separation.

In summary, for the hydrogenation reaction of 3-hydroxypropionaldehyde, the catalyst prepared by this method has the advantages of high activity, high selectivity, high stability, mild reaction conditions and relatively large catalyst particles, and is easily separated from reaction products.

Next, the technical solutions of the present application will be described below through specific embodiments. It should be understood that in one or more method steps mentioned in the present application, it is not excluded that other method steps are present before and after combined steps or other method steps can be inserted before these steps explicitly mentioned; it should also be understood that these examples are only for illustrating the present application but not limiting the scope of the present application. Furthermore, unless otherwise specified, the number of each method step is only a convenient tool for identifying each method step, and is not intended to limit the arrangement sequence of each method step or limit the implementation scope of the present application. The change or adjustment of the relative relationship shall be deemed as implementation scope of the present application without substantive change technical contents.

Examples 1-27 Raney copper catalysts and Raney copper catalysts added with metal promoters were prepared by using a conventional method. The preparation method was as follows:

A three-necked flask was taken, nitrogen was introduced from one side edge opening of the flask for purging, a burette for adding strong alkali was placed on the other side edge opening, a thermometer, a bubbling flask for testing generation of hydrogen, and a basket for supporting a catalyst were placed in the middle opening. At the same time, the basket was connected to an electric stirring shaft so that the basket rotated within the reaction flask in the process of activating the catalyst.

An appropriate amount of copper/aluminum alloy powder was taken, and the mass ratio of aluminum to copper in the copper/aluminum alloy powder was 20:80-80:20, and the preferred mass ratio was 33:66-66:33. If it was necessary to add a metal promoter, an appropriate amount of promoter metal powder M was selected and uniformly mixed with the copper/aluminum alloy powder. In a nitrogen atmosphere, the uniformly mixed metal powder was heated and melted in a melting furnace at a temperature of 500-3000° C., preferably 650-1500° C. Then, under the protection of nitrogen, the melted metal powder was cooled at room temperature to form blocks. The metal block was cracked and ground so that the size of the metal block was reduced to a proper size, the particle size was 3-140 mesh, preferably 13-35 mesh.

The obtained catalyst precursor particles were put into the basket, and the basket was guided into the middle opening of the three-necked flask. Afterwards, a large amount of deionized water and an appropriate amount of organic additives were also charged into the flask. The amount of added deionized water must allow the basket in the three-necked flask to be immersed to ensure that the catalyst precursor particles were always below the surface of the solution. At the same time, the organic additive was selected from aliphatic polyols, such as adipic polyester diol. Subsequently, the flask was sealed and purged with nitrogen to prevent the formation of an explosive gas mixture in the process of activation. The basket maintained rotation at the rotation speed of 200-1000 rpm, 40-60 wt. % sodium hydroxide aqueous solution was dropwise added into the flask within 4-6 h. After completing the addition of sodium hydroxide, the basket continued to maintain rotation and was activated until no more bubbles were generated in a bubbling bottle. After the activation was ended, the catalyst particles were taken out and washed repeatedly with deionized water until the pH value of the washing solution was less than 8.0. The obtained catalyst particles were liquid-sealed with deionized water and used for preparing 1,3-propanediol through hydrogenation of 3-hydroxypropionaldehyde.

The compositions of the catalysts in examples 1-19 are as shown in Table 1; the preparation and activation conditions of the catalysts in examples 1-19 are as shown in Table 2; the evaluation conditions and results of the catalysts in examples 1-19 are as shown in Table 3.

TABLE 1

Compositions of catalysts in examples 1-19

| Example | Compositions of catalyst | Mass ratio | Particle size of catalyst (mm) | Amount of catalyst (%) (wt.) |
|---|---|---|---|---|
| Example 1 | Al:Cu:Co | 1:1:0.2 | 0.25 | 5.0 |
| Example 2 | Al:Cu:Ni | 1:1:0.2 | 0.45 | 3.0 |
| Example 3 | Al:Cu:Fe | 1:0.5:0.2 | 0.28 | 4.0 |
| Example 4 | Al:Cu:Mo | 1:1:0.2 | 0.22 | 2.0 |
| Example 5 | Al:Cu:Ni:Mo | 1:1:0.11:0.02 | 0.32 | 2.5 |
| Example 6 | Al:Cu:Au | 1:0.85:0.005 | 0.15 | 0.9 |
| Example 7 | Al:Cu:Ag | 1:0.85:0.02 | 0.12 | 0.3 |
| Example 8 | Al:Cu:Pd | 1:0.85:0.002 | 0.1 | 0.7 |
| Example 9 | Al:Cu:Pt | 1:0.85:0.0025 | 0.16 | 0.2 |
| Example 10 | Al:Cu:Pd:Pt | 1:0.85:0.002:0.0025 | 0.14 | 0.5 |
| Example 11 | Al:Cu:Mo:Pd | 1:1:0.11:0.002 | 0.19 | 2.5 |
| Example 12 | Al:Cu:Ni | 1:1:0.15 | 0.25 | 2.5 |
| Example 13 | Al:Cu:Ni | 1:1:0.22 | 0.25 | 2.5 |
| Example 14 | Al:Cu:Ni | 1:1:0.1 | 0.25 | 2.5 |
| Example 15 | Al:Cu:Ni | 1:1:0.02 | 0.25 | 2.5 |
| Example 16 | Al:Cu:Ni | 1:1:0.2 | 0.1 | 2.5 |
| Example 17 | Al:Cu:Ni | 1:1:0.2 | 0.5 | 2.5 |
| Example 18 | Al:Cu:Ni | 1:1:0.2 | 1.0 | 2.5 |
| Example 19 | Al:Cu:Ni | 1:1:0.2 | 1.5 | 2.5 |
| Comparative example A | Al:Cu | 1:1 | 0.25 | 5.0 |
| Comparative example B | Al:Ni | 1:1 | 0.25 | 2.5 |
| Comparative example C | Al:Ni | 1:0.2 | 0.25 | 2.5 |
| Comparative example D | Al:Ni:Pd | 1:0.85:0.002 | 0.1 | 0.7 |
| Comparative example E | Al:Ni:Mo | 1:1:0.2 | 0.19 | 2.5 |
| Comparative example F | Ni:Cu | 1:1 | 0.25 | 2.5 |

TABLE 2

Preparation and activation conditions of catalysts in examples 1-19

| Example | High-temperature melting temperature/° C. | Rotation speed of basket/rpm | Activating time/h | Mass fraction of alkali solution/wt. % | Ratio of addition amount of alkali solution to particles | pH value |
|---|---|---|---|---|---|---|
| Example 1 | 750 | 500 | 4 | 40 | 3.5:1 | 7 |
| Example 2 | 900 | 650 | 5 | 48 | 3.75:1 | 7.5 |
| Example 3 | 650 | 550 | 4.5 | 45 | 3.6:1 | 7 |
| Example 4 | 950 | 600 | 4 | 42 | 3.8:1 | 8 |
| Example 5 | 850 | 600 | 4.5 | 47 | 4:1 | 7 |
| Example 6 | 1500 | 800 | 5 | 60 | 3.8:1 | 8 |
| Example 7 | 1300 | 800 | 6 | 55 | 3.75:1 | 7.5 |
| Example 8 | 1200 | 750 | 5.5 | 58 | 3.9:1 | 7.5 |
| Example 9 | 1250 | 700 | 6 | 52 | 3.85:1 | 7 |
| Example 10 | 1350 | 800 | 6 | 56 | 4:1 | 7.5 |
| Example 11 | 1050 | 650 | 5.5 | 50 | 3.8:1 | 8 |
| Example 12 | 900 | 650 | 5 | 48 | 3.75:1 | 7.5 |
| Example 13 | 3000 | 650 | 5 | 48 | 3.75:1 | 7.5 |
| Example 14 | 500 | 650 | 5 | 48 | 3.75:1 | 7.5 |
| Example 15 | 900 | 1000 | 2 | 48 | 3.75:1 | 7.5 |
| Example 16 | 900 | 200 | 8 | 48 | 3.75:1 | 7.5 |
| Example 17 | 900 | 650 | 5 | 48 | 3:1 | 7.5 |
| Example 18 | 900 | 650 | 5 | 48 | 5:1 | 7.5 |
| Example 19 | 900 | 650 | 5 | 48 | 3.75:1 | 7.5 |
| Comparative example A | 900 | 650 | 5 | 48 | 3.75:1 | 7.5 |
| Comparative example B | 900 | 650 | 5 | 48 | 3.75:1 | 7.5 |
| Comparative example C | 900 | 650 | 5 | 48 | 3.75:1 | 7.5 |
| Comparative example D | 1200 | 750 | 5.5 | 58 | 3.9:1 | 7.5 |

TABLE 2-continued

Preparation and activation conditions of catalysts in examples 1-19

| Example | High-temperature melting temperature/°C. | Rotation speed of basket/rpm | Activating time/h | Mass fraction of alkali solution/wt. % | Ratio of addition amount of alkali solution to particles | pH value |
|---|---|---|---|---|---|---|
| Comparative example E | 950 | 600 | 4 | 42 | 3.8:1 | 8 |
| Comparative example F | 900 | 650 | 5 | 48 | 3.75:1 | 7.5 |

Evaluation of Catalyst Activity:

(1) 200-300 g of 5-15 wt % 3-hydroxypropanal aqueous solution was reversely put into a 500 ml autoclave;

(2) after sealing, leak detection was conducted with nitrogen, no leakage point was ensured, then replacement was conducted for three times with nitrogen followed by hydrogen for three times, then the pressure of hydrogen was increased to 6-8 MPa, and the temperature was raised;

(3) when the temperature was raised to 70° C., stirring was started, the rotation speed was 500-1000 rpm, and the required pressure of hydrogen was maintained;

(4) the gas was replenished every 30 min, and the pressure of hydrogen was maintained to be above the reaction pressure after the reaction was ended until the pressure of hydrogen was unchanged;

(5) after the reaction temperature was dropped and the reaction was ended, the hydrogen in the autoclave was vented and replaced with nitrogen, and sampling was performed for analysis.

The specific reaction conditions and reaction results are shown in Table 3.

$$\text{Conversion rate} = \frac{\text{3-hydroxypropionaldehyde amount consumed per unit time}}{\text{Amount of 3-hydroxypropionaldehyde put into reactor per unit time}}$$

$$\text{Selectivity} = \frac{\text{Amount of 1,3-propanediol generated per unit time}}{\text{Amount of 1,3-propanediol obtained by consuming raw materials per unit time}}$$

TABLE 3

Evaluation conditions and results of catalysts in examples 1-19

| Example | Temperature/°C. | Reaction time/min | Reaction pressure/MPa | Concentration of 3-hydroxy-propionaldehyde (wt. %) | Conversion rate of 3-hydroxy-propionaldehyde/% | Selectivity of 1,3-propanediol/% |
|---|---|---|---|---|---|---|
| Example 1 | 150 | 100 | 6.0 | 5 | 98 | 99 |
| Example 2 | 125 | 110 | 3.0 | 8 | 99 | 100 |
| Example 3 | 120 | 105 | 5.0 | 12 | 92 | 99 |
| Example 4 | 80 | 120 | 10.0 | 15 | 96 | 99 |
| Example 5 | 110 | 120 | 4.5 | 12 | 97 | 99 |
| Example 6 | 85 | 65 | 3.0 | 15 | 99 | 98 |
| Example 7 | 85 | 65 | 5.0 | 15 | 99 | 96 |
| Example 8 | 40 | 75 | 9.0 | 15 | 99 | 96 |
| Example 9 | 130 | 70 | 7.0 | 10 | 99 | 99 |
| Example 10 | 95 | 60 | 6.0 | 10 | 99 | 97 |
| Example 11 | 100 | 90 | 6.0 | 15 | 100 | 100 |
| Example 12 | 100 | 110 | 6.0 | 8 | 96 | 100 |
| Example 13 | 100 | 110 | 6.0 | 8 | 94 | 100 |
| Example 14 | 100 | 110 | 6.0 | 8 | 93 | 100 |
| Example 15 | 100 | 110 | 6.0 | 8 | 93 | 100 |
| Example 16 | 100 | 110 | 6.0 | 8 | 99 | 100 |
| Example 17 | 100 | 110 | 6.0 | 8 | 99 | 100 |
| Example 18 | 100 | 110 | 6.0 | 8 | 99 | 100 |
| Example 19 | 100 | 110 | 6.0 | 8 | 99 | 100 |
| Comparative example A | 100 | 120 | 6.0 | 8 | 79 | 82 |
| Comparative example B | 100 | 120 | 6.0 | 8 | 85 | 83 |
| Comparative example C | 100 | 120 | 6.0 | 8 | 84 | 84 |
| Comparative example D | 90 | 70 | 5.0 | 15 | 85 | 84 |
| Comparative example E | 100 | 100 | 6.0 | 8 | 75 | 82 |
| Comparative example F | 100 | 120 | 6.0 | 8 | 69 | 71 |

Comparative examples A-F Raney nickel catalysts and Raney nickel catalysts added with metal molybdenum were prepared using a conventional method. The preparation method was as follows:

An appropriate amount of nickel/aluminum alloy powder was taken. The mass ratio of aluminum to nickel in the nickel/aluminum alloy powder was 33:66-66:33. If necessary, an appropriate amount of promoter metal powder M was selected and uniformly mixed with the nickel/aluminum alloy powder. In a nitrogen atmosphere, the uniformly mixed metal powder was heated and melted in a melting furnace at a temperature of 800-1200° C. The nitrogen atmosphere continued to be maintained, and the metal powder was cooled at room temperature to form a block. The metal block was cracked and ground so that the metal block was reduced to form particles with a size of 0.1-1.5 mm.

The obtained catalyst precursor particles were put into the basket body, and the basket was guided into the middle opening of the three-necked flask, and then the organic additives such as deionized water and aliphatic polyols were added into the flask together to ensure that the basket in the flask was below the liquid level. The flask was sealed and purged with nitrogen to prevent the formation of an explosive gas mixture in the process of the activation. The basket was maintained to rotate at the rotation speed of 500-700 rpm, and 40-60 wt. sodium hydroxide aqueous solution was dropwise added into the flask within 1-2 h. After completing the addition of sodium hydroxide, the basket continued to maintain rotation and was activated until no more bubbles were generated in the bubbling bottle. After activation, the catalyst particles were taken out and washed repeatedly with deionized water until the pH of the washing solution was 7.0-8.0. The obtained catalyst particles were liquid-sealed with deionized water, and were used for preparing 1,3-propanediol through hydrogenation of 3-hydroxypropionaldehyde.

In summary, the novel Raney copper catalyst provided by the present application has a good capability on hydrogenation reaction based on the synergistic effect between metal copper and different promoter metals. Compared with the Raney copper catalyst with no addition of metal promoters, when being used for preparing 1,3-propanediol through hydrogenation of 3-hydroxypropionaldehyde, this catalyst has higher activity, better selectivity, and better stability. In addition, this catalyst has relatively large particles and can be easily separated from reaction products.

The aspects, embodiments, features, and examples of the present application should be regarded as being illustrative in all aspects and are not intended to limit the present application. The scope of the present application is only defined by the claims. Without departing from the spirit and scope of the claimed application, those skilled in the art will understand other embodiments, modifications, and uses.

The use of titles and chapters in this application is not meant to limit the present application; each chapter can be applied to any aspect, embodiment or feature of this application.

Throughout the present application, where a composition is described as having, containing, or including specific components, or where a process is described as having, containing, or including specific process steps, it is expected that the composition taught in the present application is also especially composed of or consists of the described components, and the process taught in the present application is basically composed of the described process steps or a set of described process steps.

It should be understood that the order of the steps or the order of performing specific actions is not very important, as long as the teachings of the present application maintain operable. In addition, two or more steps or actions can be performed simultaneously.

In addition, the inventor of this case also referred to the above-mentioned embodiments and conducted experiments with other raw materials, process operations and process conditions described in this specification to obtain relatively ideal results.

Although the present application has been described with reference to illustrative embodiments, those skilled technicians in the field will understand that various other changes, omissions and/or additions can be made without departing from the spirit and scope of the present application, and substantive equivalents can be used to replace the elements in the embodiments. In addition, many modifications can be made without departing from the scope of the present application so that specific situations or materials adapt to the teachings of the present application. Therefore, this patent is intended to allow the present application to contain all the embodiments within the scope of the appended claims rather than limiting the present application to the specific embodiments disclosed for implementing the present application.

What is claimed is:

1. A Raney copper catalyst, comprising aluminum, copper and a metal promoter, wherein the Raney copper catalyst has a particle size of 0.1-5 mm, and wherein the metal promoter comprises a precious metal promoter and/or a non-precious metal promoter, the non-precious metal promoter comprises one or a combination of more than two of Ni, Fe, Mo and Co, and the precious metal promoter comprises one or a combination of more than two of Ag, Pd, Pt and Au.

2. The Raney copper catalyst according to claim 1, wherein a content of the metal promoter in the Raney copper catalyst is 0.1-10 wt %; and/or a mass ratio of aluminum to copper in the Raney copper catalyst is 1:(0.5-1).

3. The Raney copper catalyst according to claim 1, wherein a content of the precious metal promoter in the Raney copper catalyst is 0.1-1 wt %; and/or a content of the non-precious metal promoter in the Raney copper catalyst is 1-10 wt %.

4. The Raney copper catalyst according to claim 1, wherein when the metal promoter is selected from the non-precious metal promoter, a mass ratio of aluminum to copper to the metal promoter in the Raney copper catalyst is 1:(0.5-1):(0.02-0.22); and/or when the metal promoter is selected from the precious metal promoter, a mass ratio of aluminum to copper to the metal promoter in the Raney copper catalyst is 1:(0.5-1):(0.002-0.02); and/or when the metal promoter is selected from a combination of the precious metal promoter and the non-precious metal promoter, a mass ratio of aluminum to copper to the non-precious metal promoter to the precious metal promoter in the Raney copper catalyst is 1:(0.5-1):(0.02-0.24):(0.002-0.02).

5. A preparation method of the Raney copper catalyst according to claim 1, comprising:
performing a high-temperature melting on a mixture containing a copper/aluminum alloy and the metal promoter in a protective atmosphere, and then standing at room temperature to obtain a mixed metal cured compound;
smashing the mixed metal cured compound to obtain a catalyst precursor; and activating the catalyst precursor to obtain the Raney copper catalyst.

6. The preparation method according to claim 5, wherein a mass ratio of aluminum to copper in the copper/aluminum alloy is 20:80-80:20; and/or a temperature of high-temperature melting is 500-3000° C.; and/or the protective atmosphere comprises a nitrogen atmosphere;

and/or the step of smashing comprises: cracking and grounding the mixed metal cured compound to a selected size to obtain the catalyst precursor; wherein the selected size is 3-140 mesh.

7. The preparation method according to claim 5, wherein the step of activating comprises:

placing a reaction basket body loaded with the catalyst precursor into a reaction container, then adding water and an organic additive into the reaction container, then sealing the reaction container, and maintaining the reaction basket body to vertically rotate;

adding an alkali aqueous solution into the reaction container dropwise, and meanwhile the reaction basket body continues to be maintained to vertically rotate to activate at room temperature;

wherein the organic additive comprises aliphatic polyhydric alcohols, and an aliphatic polyhydric alcohol is adipic polyester diol;

wherein in the reaction container, water is added in an amount at least submerging a surface of the catalyst precursor;

a rotation speed of the reaction basket body is 200-1000 rpm;

an activating time is 2-8 hours;

an alkali contained in the alkali aqueous solution comprises sodium hydroxide and/or potassium hydroxide;

a mass fraction of the alkali aqueous solution is 40-60%;

a mass ratio of alkali aqueous solution to the mixed metal cured compound is 3:1-5:1;

and/or, after the step of activating is ended, the preparation method further comprises: taking out the Raney copper catalyst, and washing the Raney copper catalyst with water to a pH value of 7-8.

8. The preparation method according to claim 5, wherein a content of the metal promoter in the Raney copper catalyst is 0.1-10 wt %; and/or a mass ratio of aluminum to copper in the Raney copper catalyst is 1:(0.5-1).

9. The preparation method according to claim 5, wherein a content of the precious metal promoter in the Raney copper catalyst is 0.1-1 wt %; and/or a content of the non-precious metal promoter in the Raney copper catalyst is 1-10 wt %.

10. The preparation method according to claim 5, wherein when the metal promoter is selected from the non-precious metal promoter, a mass ratio of aluminum to copper to the metal promoter in the Raney copper catalyst is 1:(0.5-1):(0.02-0.22); and/or when the metal promoter is selected from the precious metal promoter, a mass ratio of aluminum to copper to the metal promoter in the Raney copper catalyst is 1:(0.5-1):(0.002-0.02); and/or when the metal promoter is selected from a combination of the precious metal promoter and the non-precious metal promoter, a mass ratio of aluminum to copper to the non-precious metal promoter to the precious metal promoter in the Raney copper catalyst is 1:(0.5-1):(0.02-0.24):(0.002-0.02).

11. A method of using the Raney copper catalyst according to claim 1, comprising using the Raney copper catalyst in preparation of 1,3-propanediol through a hydrogenation of 3-hydroxypropionaldehyde.

12. The method according to claim 11, wherein a content of the metal promoter in the Raney copper catalyst is 0.1-10 wt %; and/or a mass ratio of aluminum to copper in the Raney copper catalyst is 1:(0.5-1).

13. The method according to claim 11, wherein a content of the precious metal promoter in the Raney copper catalyst is 0.1-1 wt %; and/or a content of the non-precious metal promoter in the Raney copper catalyst is 1-10 wt %.

14. The method according to claim 11, wherein when the metal promoter is selected from the non-precious metal promoter, a mass ratio of aluminum to copper to the metal promoter in the Raney copper catalyst is 1:(0.5-1):(0.02-0.22); and/or when the metal promoter is selected from the precious metal promoter, a mass ratio of aluminum to copper to the metal promoter in the Raney copper catalyst is 1:(0.5-1):(0.002-0.02); and/or when the metal promoter is selected from a combination of the precious metal promoter and the non-precious metal promoter, a mass ratio of aluminum to copper to the non-precious metal promoter to the precious metal promoter in the Raney copper catalyst is 1:(0.5-1):(0.02-0.24):(0.002-0.02).

15. A method for preparing 1,3-propanediol, comprising:
carrying out a hydrogenation reaction on a reaction system containing the Raney copper catalyst according to claim 1 and an aqueous solution of 3-hydroxypropionaldehyde in a hydrogen atmosphere to prepare the 1,3-propanediol;
wherein a content of the Raney copper catalyst in the reaction system is 0.2-5.0 wt %;
process conditions of the hydrogenation reaction are as follows: a temperature of the hydrogenation reaction is 40-150° C., a time of the hydrogenation reaction is 60-120 minutes, a pressure of the hydrogenation reaction is 3.0-10.0 MPa, and a concentration of the aqueous solution containing the 3-hydroxypropionaldehyde is 5-15 wt %.

16. The method according to claim 15, wherein a content of the metal promoter in the Raney copper catalyst is 0.1-10 wt %; and/or a mass ratio of aluminum to copper in the Raney copper catalyst is 1:(0.5-1).

17. The method according to claim 15, wherein a content of the precious metal promoter in the Raney copper catalyst is 0.1-1 wt %; and/or a content of the non-precious metal promoter in the Raney copper catalyst is 1-10 wt %.

* * * * *